United States Patent
Heuer

(10) Patent No.: US 9,447,782 B2
(45) Date of Patent: Sep. 20, 2016

(54) COMPRESSOR AND METHOD FOR COMPRESSING TECHNICAL GASES

(75) Inventor: Lutz Heuer, Dormagen (DE)

(73) Assignee: LANXESS Deutschland GmbH, Cologne (DE)

( * ) Notice: Subject to any disclaimer, the term of this patent is extended or adjusted under 35 U.S.C. 154(b) by 216 days.

(21) Appl. No.: 13/993,451

(22) PCT Filed: Dec. 13, 2011

(86) PCT No.: PCT/EP2011/072649
§ 371 (c)(1),
(2), (4) Date: Aug. 13, 2013

(87) PCT Pub. No.: WO2012/080277
PCT Pub. Date: Jun. 21, 2012

(65) Prior Publication Data
US 2013/0323087 A1  Dec. 5, 2013

(30) Foreign Application Priority Data
Dec. 13, 2010  (EP) .................................... 10194703

(51) Int. Cl.
*F04B 19/20* (2006.01)
*F04B 39/00* (2006.01)
(Continued)

(52) U.S. Cl.
CPC .......... *F04B 39/0011* (2013.01); *B01D 53/04* (2013.01); *B01D 53/047* (2013.01); *B01D 53/14* (2013.01); *B01D 53/18* (2013.01); *B01D 53/74* (2013.01); *B01D 53/75* (2013.01); *C07B 63/00* (2013.01); *F04B 37/04* (2013.01);
(Continued)

(58) Field of Classification Search
CPC ........ F04B 37/02; F04B 37/04; F04B 39/16; F04B 53/20; F04B 39/0011; B01D 53/0407; B01D 53/047; B01D 53/14; B01D 53/74; B01D 53/04; B01D 53/18; B01D 53/75; B01D 2252/20473; B01D 2252/30; B01D 2252/2056
See application file for complete search history.

(56) References Cited

U.S. PATENT DOCUMENTS 4,060,912 A * 12/1977 Black .............................. 34/341
5,871,563 A   2/1999 Roth et al.
(Continued)

FOREIGN PATENT DOCUMENTS

| CN | 10152519 A | 1/2010 |
| CN | 101634513 A | 1/2010 |

(Continued)

OTHER PUBLICATIONS

International Search Report PCT/EP2011/027649 dated Mar. 12, 2012 (6 pages).

*Primary Examiner* — Bryan Lettman

(57) ABSTRACT

A compressor system and method for the isothermal compression of industrial gases includes a compression cylinder into which an industrial gas having impurities can be introduced and compressed via a displacement fluid, and an expansion space for the desorption of impurities from at least part of the displacement fluid after the displacement fluid sorbs impurities from the gas during compression in the compression cylinder. The displacement fluid may compress the gas and sorb contaminants from the gas, and following the compression, at least a portion of the displacement fluid may be conducted to an expansion chamber to desorb the impurities from the fluid and remove the impurities from the system.

18 Claims, 1 Drawing Sheet

(51) Int. Cl.
    *F04B 37/04*     (2006.01)
    *F04B 39/16*     (2006.01)
    *F04B 53/20*     (2006.01)
    *B01D 53/04*     (2006.01)
    *B01D 53/047*    (2006.01)
    *B01D 53/14*     (2006.01)
    *B01D 53/18*     (2006.01)
    *B01D 53/74*     (2006.01)
    *B01D 53/75*     (2006.01)
    *C07B 63/00*     (2006.01)
    *F04B 37/20*     (2006.01)
    *F04F 1/06*     (2006.01)
    *F17C 5/00*     (2006.01)
    *F17C 5/02*     (2006.01)

(52) U.S. Cl.
    CPC .............. *F04B 37/20* (2013.01); *F04B 39/16* (2013.01); *F04B 53/20* (2013.01); *F04F 1/06* (2013.01); *F17C 5/00* (2013.01); *F17C 5/02* (2013.01); *B01D 2252/2056* (2013.01); *B01D 2252/20473* (2013.01); *B01D 2252/30* (2013.01)

(56) References Cited

U.S. PATENT DOCUMENTS 6,156,100 A * 12/2000 Conrad et al. .................... 95/98
6,162,283 A     12/2000 Conrad et al.
2010/0071698 A1* 3/2010 Kiritake .................. 128/205.27

FOREIGN PATENT DOCUMENTS

| DE | 4327524 A1 | 2/1995 | |
|----|----|----|----|
| DE | 102006014335 A1 | 10/2007 | |
| EP | 1679307 A1 | 7/2006 | |
| WO | 9604978 A1 | 2/1996 | |
| WO | WO2008136540 | * 11/2008 | ............ A61M 16/10 |

* cited by examiner

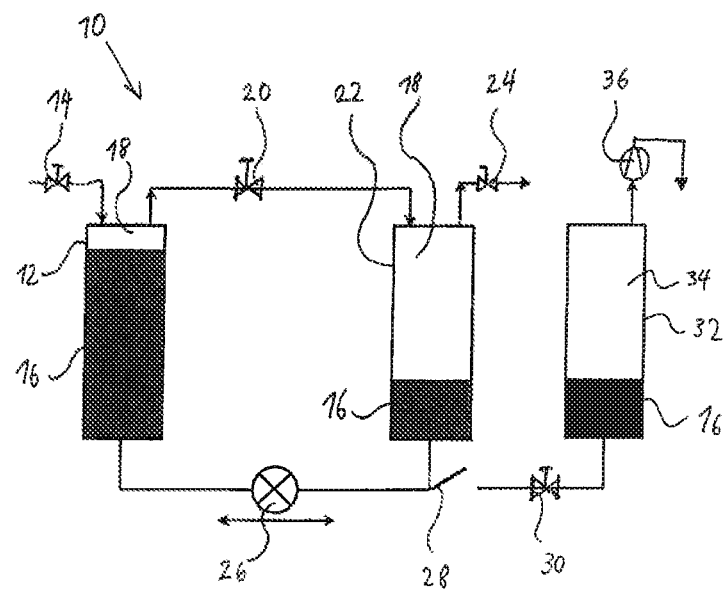

COMPRESSOR AND METHOD FOR COMPRESSING TECHNICAL GASES

The present invention relates to a compressor and to a method, with the aid of which, in particular, essentially isothermal compression of industrial gases can take place.

In order to compress gases essentially isothermally, it is known, in a compressor, to compress the gas introduced into a compression cylinder not by means of a piston, but instead by means of a displacement fluid, so that the heat occurring during the compression of the gas can be absorbed by the displacement fluid and be conducted away from the gas within the displacement fluid. However, the industrial gases used on an industrial scale are often gases which have been recovered in circulatory streams occurring in chemical processes and, on account of the chemical equilibria which are established, are laden, in particular, with gaseous impurities. A typical industrial gas therefore has, in addition to a desired main component, one or more, in particular, gaseous impurities. These impurities may be absorbed by the displacement fluid, so that, because of this contamination, the displacement fluid may change its chemical and physical properties and, after certain ageing, has to be exchanged. In order to avoid or at least delay the exchange of the displacement fluid, it is necessary to subject the industrial gas, before compression, to a gas scrub which, however, is cost-intensive and is effective to only an inadequate extent.

The object of the invention is to provide a compressor and a method for the, in particular, isothermal compression of industrial gases, which are less sensitive to impurities of the industrial gases to be compressed.

The object is achieved, according to the invention, by means of a compressor for the, in particular, isothermal compression of industrial gases, with a compression cylinder, into which an industrial gas having impurities can be introduced, and a displacement fluid capable of being introduced into the compression cylinder by means of a compressor pump, the displacement fluid having higher solubility for at least one impurity of the industrial gas than for a main component of the industrial gas, an expansion space for the desorption of the impurity from at least part of the displacement fluid being provided, a purge pump for the discharge of impurities which have assumed the gas phase being connected to the expansion space.

The further subject of the invention is a method for the, in particular, isothermal compression of industrial gases, in which an industrial gas which has a main component and at least one impurity is delivered to a compressor according to the invention, and the industrial gas is compressed by the displacement fluid, at the same time at least part of the impurity being absorbed by the displacement fluid, and subsequently the absorbed impurity is at least partially desorbed from at least part of the displacement fluid into the gas phase and is discharged.

The compressor according to the invention for the, in particular, isothermal compression of industrial gases has a compression cylinder, into which an industrial gas having impurities can be introduced, and a displacement fluid capable of being introduced into the compression cylinder by means of a compressor pump, the displacement fluid having higher solubility for at least one impurity of the industrial gas than for a main component of the industrial gas. According to the invention, an expansion space for the desorption of the impurity from at least part of the displacement fluid is provided, a purge pump for the discharge of impurities which have assumed the gas phase being connected to the expansion space.

By means of the expansion space which is provided for the compressor in addition to the compression cylinder and is separated from the compression cylinder, the impurities absorbed by the displacement fluid can be separated again in a controlled atmosphere, so that ageing of the displacement fluid as a result of progressive contamination with absorbed impurities can be avoided or at least markedly reduced. The compressor is consequently less sensitive to impurities of the industrial gases to be compressed, without an additionally preceding gas scrub being necessary. At the same time, the compressor can also perform, in addition to the compression function, the function of separating impurities from the industrial gas, so that, preferably, the chemical and physical properties of the displacement fluid can be selected even for the purpose of the absorption of impurities from the industrial gas. Absorption of impurities by the displacement fluid is therefore not to be avoided, but is even to be brought about deliberately. The desorption of the impurities absorbed by the displacement fluid may in this case be integrated into the compressor, so that, for example, the expansion space can be filled and/or emptied with the aid of the compressor pump which is in any case provided.

The compressor pump may, for example, pump the displacement fluid out of a reservoir into the compression cylinder, in order to compress the previously sucked-in and/or pumped-in industrial gas. When the filling level of the displacement fluid in the compression cylinder is sufficiently high, for example, the compressed gas may leave the compression cylinder at the higher pressure level via the opening of an outlet valve. In this case, it is possible to continue to fill the compression cylinder with the displacement fluid, so that the displacement fluid flowing in can press a correspondingly large volume of the compressed gas out of the compression cylinder. Subsequently, the compressor pump may change its pumping direction and, in particular, after closing of the outlet valve, pump the displacement fluid out of the compression cylinder. While the displacement fluid is being pumped out, for example, an inlet valve may be opened, so that an industrial gas to be compressed can be sucked into the compression cylinder with the aid of the vacuum occurring by the displacement fluid being pumped out. In particular, at least part of the pumped-out displacement fluid may preferably be pumped into the expansion space with the aid of the compressor pump, so that an impurity absorbed during compression can be desorbed again. The purge pump can discharge the gas phase present in the expansion space, together with the desorbed impurities, and set as low a pressure level as possible within the expansion space. It is also possible to leave the displacement fluid in the expansion space for a plurality of compression cycles, so that, depending on the pumping capacity of the purge pump, an especially low pressure level can be reached which lies only slightly above the vapor pressure of the displacement fluid or even close to a vacuum. For subsequent compression, the compressor pump may pump at least part of the displacement fluid purified by desorption into the compression cylinder. The at least partial purification of the displacement fluid improves the absorbency, so that a correspondingly larger substance amount of impurities can be dissolved in the displacement fluid and separated via desorption.

In particular the expansion space can be filled only partially with the displacement fluid for the desorption of the impurities. As a result, in the expansion space, a gas phase remains which the impurities dissolved in the displacement fluid can assume. At the same time, a high pressure level can be avoided, and with the aid of the purge pump as low a pressure level as possible can be maintained within the expansion space. In particular, the situation can be avoided where the purge pump unintentionally discharges displacement fluid out of the expansion space.

Preferably, when the displacement fluid is introduced, the expansion space has an expansion pressure $p_E$ and the compressor cylinder, in the essentially emptied state, has an intake pressure $p_A$, the expansion pressure $p_E$ being lower than the intake pressure $p_A$. in particular, $0.000001 \leq p_E/p_A \leq 0.9$, preferably $0.0005 \leq p_E/p_A \leq 0.7$, further preferably $0.01 \leq p_E/p_A \leq 0.5$ and especially preferably $0.2 \leq p_E/p_A \leq 0.4$. As a result, a comparatively low pressure is established in the expansion space and promotes the desorption of the absorbed impurities. At the same time, in the compression cylinder, a comparatively high pressure may prevail, which promotes absorption and also prevents or at least keeps low desorption in the compression cylinder.

Especially preferably, when the displacement fluid is introduced, the expansion space has an expansion pressure $p_E$, the expansion pressure $p_E$ being 10 hPa$\leq p_E \leq$1000 hPa, in particular 50 hPa$\leq p_E \leq$800 hPa, preferably 100 hPa$\leq p_E \leq$600 hPa and especially preferably 200 hPa$\leq p_E \leq$400 hPa. Such pressures can be achieved in the expansion space by the purge pump comparatively simply, and at these pressures desorption of the impurities can be achieved to a comparatively great extent.

In particular, the expansion space has a temperature $T_E$ and the compression cylinder a compressor temperature $T_V$, where 1 K$\leq(T_E-T_V)\leq$100 K, in particular 5 K$\leq(T_E-T_V)\leq$50 K and preferably 10 K$\leq(T_E-T_V)\leq$30K applies. Such temperature differences promote the absorption of the impurities within the compression cylinder and the desorption of the impurities in the expansion space. At the same time, such temperature differences can be handled comparatively easily in order to set a defined temperature for the displacement fluid. Particularly when essentially isothermal compression is to be achieved, the displacement fluid heated by the absorbed compression heat may be cooled with the aid of a heat exchanger, while part of this discharged heat may be delivered, for example, to the expansion space. Furthermore, the heated displacement fluid from the expansion space may likewise be delivered to the cooling side of the same heat exchanger.

Preferably, the purge pump is configured as a vacuum pump. This makes it possible to set an especially low pressure level within the expansion space. Furthermore, it is possible to discharge an especially large number of molecules of the desorbed impurities via the purge pump. On account of the particular type of construction of the vacuum pump, a return flow back into the expansion space can be avoided, so that an unintentional pressure rise within the expansion space due to leakage flows can be avoided.

In a preferred embodiment, at least one additional cylinder for the stepped compression of the industrial gas is provided, the compressor pump being connected to the compression cylinder, to the additional cylinder and to the expansion space in such a way that, when the compression cylinder is being emptied, both the additional cylinder and the expansion space can be filled with the aid of the compressor pump. In particular, a plurality of additional cylinders are connected in series, in order to achieve an especially high pressure level for the compressed gas by means of stepped compression. For example, three to seven additional cylinders connected in series are provided. To increase the volume flow, a plurality of compression cylinders or additional cylinders may also be connected in parallel for each step. In particular, not only additional compression, but also additional absorption of impurities, may take place in the additional cylinder with the aid of the displacement fluid. Preferably, the additional cylinder has a lower volume than the compression cylinder or a previous additional cylinder. It is thereby possible to provide a lower residual volume for the compressed gas in the additional cylinder and/or to pump in a lower volume of displacement fluid, so that the differential volume of the displacement fluid can be conducted into the expansion space. For this purpose, it is possible to fill both the additional cylinder and the expansion space by means of the same compressor pump, in which case this filling may take place simultaneously with the emptying of the compression cylinder.

In particular, the displacement fluid has, at 23° C. and 1000 hPa, a vapor pressure $p_V$ of $p_V \leq$1 hPa, in particular $p_V \leq$0.1 hPa, preferably $p_V \leq$0.01 hPa and especially preferably $p_V \leq$0.001 hPa. In particular, the vapor pressure lies below the measurement limit of laboratory measuring instruments. Since the displacement fluid has essentially no vapor pressure or the vapor pressure is negligibly low, evaporation of the displacement fluid in the expansion space can be avoided. Even in the case of especially low pressures within the expansion space, evaporation of the displacement fluid can be largely avoided, so that essentially only the absorbed impurities assume the gas phase.

Suitable displacement fluids are, in particular, ionic fluids. Ionic fluids are to be understood in the context of the invention to mean compounds which have at least one cation or one cationic group and at least one anion or one anionic group, but overall are charge-neutral, and are liquid at 23° C. and 1000 hPa. Unintentional evaporation of the displacement fluid can consequently be largely avoided.

Preferred ionic fluids are those which have an organic cation and an organic anion.

A suitable displacement fluid designated as operation fluid is described, for example, in claim 7 of DE 10 2006 014 335 A1, to the contents of which reference is hereby made as part of the invention. Preferably, the displacement fluid used is 1-butyl-2,3-dimethylimidazoliumbis(trifluoromethylsulfonyl)imide and/or 1-butyl-3-ethyl-2-dimethylimidazoliumbis(trifluoromethylsulfonyl)imide.

The displacement fluid preferably has a viscosity lower than 1200 mPas at −10° C. and higher than 10 mPas at +100° C. In a preferred embodiment, additives, for example water and/or methane, which can evaporate more easily in comparison with the rest of the displacement fluid are admixed to the displacement fluid, so that the displacement fluid can be cooled as a result of the evaporation of the additives.

The invention relates, furthermore, to a method for the, in particular, isothermal compression of industrial gases, in which an industrial gas which has a main component and at least one impurity is delivered to a compressor which may be designed and developed, as described above. In addition, the industrial gas is compressed by the displacement fluid, at the same time at least part of the impurity being absorbed by the displacement fluid. Subsequently, the absorbed impurity is at least partially desorbed from at least part of the displacement fluid into the gas phase and is discharged. By means of the expansion space provided for the compressor in addition to the compression cylinder and separated from the compression cylinder, the impurities absorbed by the displacement fluid can be separated again in a controlled atmosphere, so that ageing of the displacement fluid as a result of progressive contamination by absorbed impurities can be avoided or at least markedly reduced. The method is consequently less sensitive to impurities of the industrial gases to be compressed. The method may, in particular, be designed and developed, as explained above by means of the compressor according to the invention.

In particular, during the desorption of the absorbed impurity, the impurity is evaporated as a result of a pressure drop and/or temperature rise. A gas scrub or extraction is not necessary.

Preferably, when the compression cylinder is being emptied, both an additional cylinder for the stepped compression of the industrial gas and the expansion space are simultaneously filled with the emptied displacement fluid. This makes it possible to carry out the emptying of the compression cylinder and the filling of the additional cylinder and of the expansion space by means of a common compressor pump. Additional pumps and control logics co-ordinating the operation of the various pumps are not necessary.

Especially preferably, the expansion space is filled only partially for the desorption of the impurity into the gas phase. As a result, in the expansion space, a gas phase remains which the impurities dissolved in the displacement fluid can assume. At the same time, a high pressure level can be avoided and as low a pressure level as possible can be maintained within the expansion space with the aid of the purge pump. In particular, the situation can be avoided where the purge pump unintentionally discharges displacement fluid out of the expansion space.

In particular, displacement fluid flowing in displaces the desorbed impurity out of the expansion space. The discharge of the desorbed impurities out of the expansion space can thereby be improved. In particular, the residual volume for the gas phase can be reduced when the purge pump has already reached a defined especially low pressure, so that the volume flow of the purge pump and the efficiency of the purge pump can be improved, without having to take into account significant absorption of the previously desorbed impurities. The volume flow of the displacement fluid flowing in can be adapted, in particular, to the volume flow and/or the pressure in the expansion space.

The invention is explained below, by way of example, by means of a preferred exemplary embodiment, with reference to the accompanying drawing in which:

FIG. 1: shows a schematic circuit diagram of a compressor according to the invention.

The compressor 10 illustrated in FIG. 1 has a compression cylinder 12 which can be filled via an inlet valve 14 with an industrial gas having impurities. Subsequently, the inlet valve 14 can be closed and a displacement fluid which is in the form of an ionic fluid 16 and compresses the industrial gas to a residual volume 18 can be introduced. In this case, the ionic fluid 16 can absorb compression heat occurring and absorb impurities. At a sufficiently high pressure, an outlet valve 20 connected to the compression cylinder 12 can be opened. In the present exemplary embodiment, in a further compression step the compressed ns can be delivered to an additional cylinder 22 where the gas can be compressed anew to a residual volume 18 with the aid of the ionic fluid 16. After renewed compression, the gas can be delivered via a further outlet valve 24 to a reservoir, a consumer or a further additional cylinder 22.

With the aid of a compressor pump 26, the compressor cylinder 22 and/or the additional cylinder 22 can be filled and/or emptied. In the exemplary embodiment illustrated, a branching valve 28 is provided between the compressor pump 26 and the additional cylinder 22 and connects to an expansion space 32 via a throttle valve 30. The compressor pump 26 can pump the ionic fluid 16 charged with absorbed impurities into the expansion space 32 where the ionic fluid 16 is exposed to a markedly lower pressure on account of the throttle valve 30. As a result, the absorbed impurities within the expansion space 32 can assume the gas phase 34, no that the impurities can be separated with the aid of a purge pump configured as a vacuum pump 36. Subsequently, the ionic fluid 16 purified in the expansion space 32 can be pumped out of the expansion space 32 with the aid of the compressor pump 26 and used again for compression in the compression cylinder 12 and/or in the additional cylinder 22, while impurities can be absorbed more effectively due to the purification of the ionic fluid 16, without the ionic fluid 16 having to be exchanged on account of ageing effects and changing chemical and/or physical properties.

What is claimed is:

1. A compressor system for an isothermal compression of industrial gases, wherein the industrial gases have a main gas component and an impurity component, the compressor system comprising:
    with a compression cylinder configured for receiving the industrial gases having the impurity component;
    a displacement fluid pumped into the compression cylinder to compress the industrial gases, and pumped out of the compression cylinder to decompress the industrial gases, wherein the displacement fluid is selected to have a higher solubility for at least one impurity of the impurity component of the industrial gases than for the main gases component of the industrial gases to sorb the at least one impurity from the industrial gases in the compression cylinder;
    a pump for pumping the displacement fluid into and out of the compression cylinder;
    an additional tank for receiving at least a portion of the displacement fluid containing the at least one impurity, wherein the additional tank comprises an expansion space for a desorption of the at least one impurity from the displacement fluid; and
    a purge pump for discharging of the desorbed at least one impurity from the expansion space.

2. The compressor system as claimed in claim 1, wherein the expansion space is configured to be filled only partially with the displacement fluid for the desorption of the at least one impurity.

3. The compressor system as claimed in claim 1 or 2, wherein, expansion space has an expansion pressure $p_E$ when the displacement fluid is introduced into the expansion space, and the compressor cylinder has an intake pressure $p_A$ in an essentially empty state, wherein the expansion pressure $p_E$ is lower than the intake pressure $p_A$.

4. The compressor system as claimed in claim 2, wherein the expansion space has an expansion pressure $p_E$ when the displacement fluid is introduced into the expansion space, and the compressor cylinder has an intake pressure $p_A$ in an empty state, wherein:
    the expansion pressure $p_E$ is lower than the intake pressure $p_A$, and $0.000001 \leq p_E/p_A \leq 0.9$; and
    the expansion pressure $p_E$ is 10 hPa $\leq p_E \leq$ 1000 hPa.

5. The compressor system as claimed in claim 4, wherein:
    $0.01 \leq p_E/p_A \leq 0.5$;
    100 hPa $\leq p_E \leq$ 600 hPa;
    the expansion space has a temperature $T_E$ and the compression cylinder a compressor temperature $T_V$, where 5 K $\leq (T_E - T_V) \leq$ 50 K; and
    the displacement fluid has, at 23° C. and 1000 hPa, a vapor pressure $p_V$ of $p_V \leq 0.01$ hPa.

6. The compressor system as claimed in claim 5, wherein:
$0.2 \leq p_E/p_A \leq 0.4$;
$200 \text{ hPa} \leq p_E \leq 400 \text{ hPa}$;
$10 \text{ K} \leq (T_E - T_V) \leq 30 \text{ K}$; and
$p_V \leq 0.001 \text{ hPa}$.

7. The compressor system as claimed in claim 1, wherein, the expansion space has an expansion pressure $p_E$ when the displacement fluid is introduced into the expansion space, and the expansion pressure $p_E$ is $10 \text{ hPa} \leq p_E \leq 1000 \text{ hPa}$.

8. The compressor system as claimed in claim 1, wherein the expansion space has a temperature $T_E$ and the compression cylinder a compressor temperature $T_V$, where $1 \text{K} \leq (T_E - T_V) \leq 100 \text{ K}$.

9. The compressor system as claimed in claim 1, wherein the purge pump is a vacuum pump.

10. The compressor system as claimed in claim 1, further comprising at least one additional cylinder for a stepped compression of the industrial gases, wherein the compressor pump is connected to the compression cylinder, to the additional cylinder and to the expansion space for moving the displacement fluid from the compression cylinder to both the additional cylinder and the expansion space.

11. The compressor system as claimed in claim 1, wherein the displacement fluid has, at 23° C. and 1000 hPa, a vapor pressure $p_V$ of $p_V \leq 1 \text{ hPa}$.

12. The compressor as claimed in claim 1, wherein the displacement fluid comprises at least one ionic fluid.

13. The compressor as claimed in claim 12, characterized in that the displacement fluid comprises at least one of 1-butyl-2,3-dimethylimidazoliumbis(trifluoromethylsulfonyl)imide and 1-butyl-3-ethyl-2-dimethylimidazoliumbis(trifluoromethylsulfonyl)imide.

14. A method for an isothermal compression of industrial gases having a main gas component and an impurity component, the method comprising:
delivering the industrial gases to a compressor system comprising:
a compression cylinder for receiving the industrial gases having the impurity component;
a displacement fluid for being pumped into and out of the compression cylinder, wherein the displacement fluid is selected to have a higher solubility for at least one impurity of the impurity component of the industrial gases than for the main gases component of the industrial gases;
a pump for pumping the displacement fluid into out of the compression cylinder;
an additional tank for receiving at least a portion of the displacement fluid containing the at least one impurity of the impurity component, wherein the additional tank comprises an expansion space for a desorption of the at least one impurity of the impurity component from the displacement fluid; and
a purge pump for discharging of desorbed impurities from the expansion space;
compressing the industrial gases in the compression cylinder by adding the displacement fluid, and at the same time, sorbing at least part of the impurity component from the industrial gases by the displacement fluid,
pumping the displacement fluid from the compression cylinder to the additional tank;
subsequently at least partially desorbing the sorbed impurity component from at least part of the displacement fluid into a gas phase and discharging the gas phase impurity component from the additional tank.

15. The method as claimed in claim 14, further comprising, during the desorption of the sorbed impurity component, evaporating the impurity as a result of at least one of a pressure drop and a temperature rise.

16. The method as claimed in claim 14 or 15, further comprising, when pumping the displacement fluid from the compression cylinder, simultaneously filling both an additional cylinder for a stepped compression of the industrial gases, and the expansion space with the displacement fluid pumped from the compression cylinder.

17. The method as claimed in claim 14, further comprising filling in whir the expansion space only partially for the desorption of the impurity component into the gas phase.

18. The method as claimed in claim 14, further comprising displacing the desorbed impurity component out of the expansion space by flowing the displacement fluid into the expansion space.

* * * * *